United States Patent
Molloy

(10) Patent No.: US 10,542,753 B2
(45) Date of Patent: Jan. 28, 2020

(54) COMPOSITIONS FOR IMPROVING BUDBREAK AND FLOWERING

(71) Applicant: Zelam Limited, New Plymouth (NZ)

(72) Inventor: Christopher Molloy, New Plymouth (NZ)

(73) Assignee: Zelam Limited, Bell Block, New Plymouth (NZ)

( * ) Notice: Subject to any disclaimer, the term of this patent is extended or adjusted under 35 U.S.C. 154(b) by 32 days.

(21) Appl. No.: 15/539,196

(22) PCT Filed: Mar. 1, 2016

(86) PCT No.: PCT/NZ2016/050031
§ 371 (c)(1),
(2) Date: Jun. 23, 2017

(87) PCT Pub. No.: WO2016/140580
PCT Pub. Date: Sep. 9, 2016

(65) Prior Publication Data
US 2017/0360036 A1    Dec. 21, 2017

(30) Foreign Application Priority Data
Mar. 3, 2015 (NZ) .................................... 705626

(51) Int. Cl.
| | | |
|---|---|---|
| A01N 37/40 | (2006.01) | |
| C05C 1/00 | (2006.01) | |
| C05C 3/00 | (2006.01) | |
| C05G 3/02 | (2006.01) | |
| C05C 9/00 | (2006.01) | |
| A01N 25/30 | (2006.01) | |
| A01N 3/00 | (2006.01) | |
| A01N 25/04 | (2006.01) | |
| A01N 33/08 | (2006.01) | |

(52) U.S. Cl.
CPC ............ *A01N 37/40* (2013.01); *A01N 3/00* (2013.01); *A01N 25/04* (2013.01); *A01N 25/30* (2013.01); *A01N 33/08* (2013.01); *C05C 1/00* (2013.01); *C05C 3/00* (2013.01); *C05C 9/005* (2013.01); *C05G 3/02* (2013.01)

(58) Field of Classification Search
CPC ......... A01N 37/40; A01N 33/08; A01N 3/00; A01N 25/04; A01N 25/30; C05C 1/00; C05C 3/00; C05C 9/005; C05G 3/02
See application file for complete search history.

(56) References Cited

U.S. PATENT DOCUMENTS

| | | |
|---|---|---|
| 5,693,592 A | 12/1997 | Illingworth |
| 5,811,290 A | 9/1998 | Varadaraj et al. |
| 5,885,932 A | 3/1999 | Parr et al. |
| 2014/0179520 A1 | 6/2014 | Haschemeyer |

FOREIGN PATENT DOCUMENTS

| | | |
|---|---|---|
| EP | 1189513 B1 | 5/2006 |
| WO | WO 97/24926 | 7/1997 |
| WO | WO 2005/013692 | 2/2005 |

OTHER PUBLICATIONS

PCT/NZ2016/050031 International Search Report and Written Opinion, dated May 24, 2016, 10 pages.
Mariana Rivas-San Vicente and Javier Plasencia, Salicylic acid beyond defence: its role in plant growth and development, Journal of Experimental Botany, vol. 62, No. 10, pp. 3321-3338, dated Feb. 28, 2011.
R H Biggs: Screening Chemicals for the Capacity to Modify Bud Dormancy of Peaches, Proceedings of the Florida State Horticultural Society, vol. 79, pp. 383-386, XP055272576, p. 385, table 1, dated Jan. 1, 1966.
Salinero et al., 2009, Phenological growth stages of kiwifruit (*Actinidia deliciosa* "Hayward"), Scientia Horticulturae 121, 27-31.

*Primary Examiner* — John Pak
*Assistant Examiner* — Andriae M Holt
(74) *Attorney, Agent, or Firm* — Dority & Manning, P.A.

(57) ABSTRACT

The invention relates to a composition formulated to produce improved budbreak, flowering and disease resistance in perennial fruit crops and/or ornamental trees, comprising: (a) one or more compounds represented by the structure: in which R' is OH or OCOCH$_3$, and R" is H, a monovalent cation, any C1-C10 alkyl group (saturated, unsaturated, linear or branched), any C7-C10 alkaryl group, or a phenyl group; and (b) an alkoxylated amine represented by the structure: in which A is selected from N, N$^1$R$_1$, or N→O, and wherein R$_1$ is H, methyl or benzyl, R$_2$ is any C8-C22 alkyl group (saturated, unsaturated, linear or branched), R$_3$ is any C2-C4 alkyl group (linear or branched), x is in the range of 0 to 4 and y+z is in the range of 2 to 50. A method of use is also included, as is a method for preparing the composition.

17 Claims, 8 Drawing Sheets

Figure 1. Progression of budbreak in Trial 1.
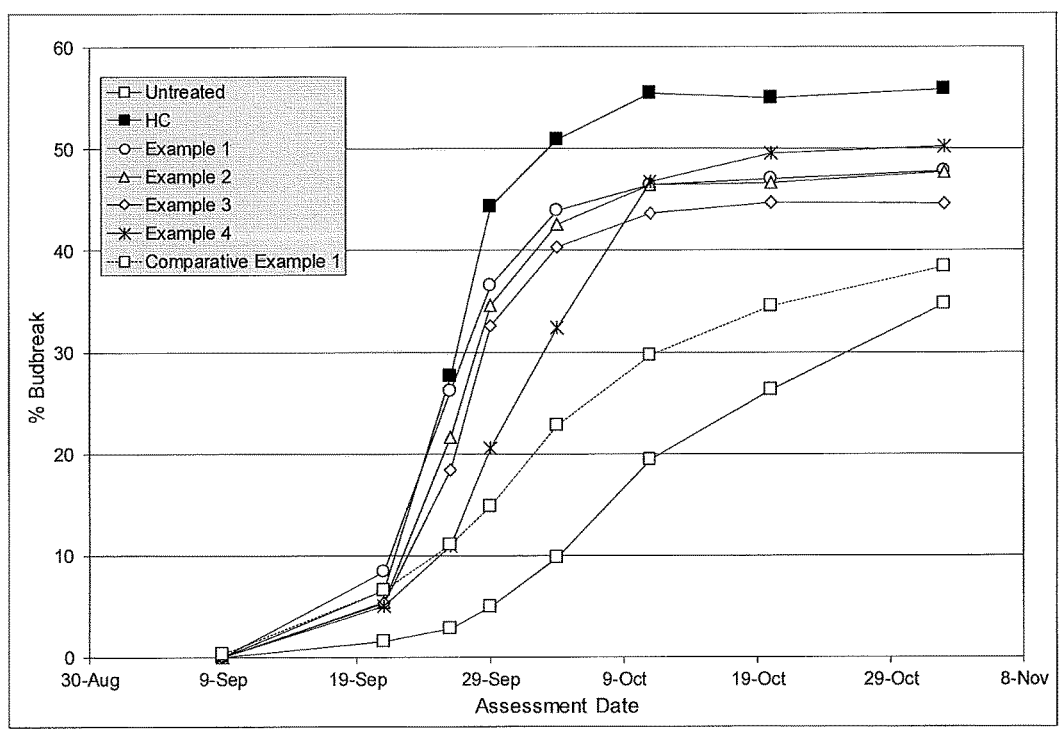

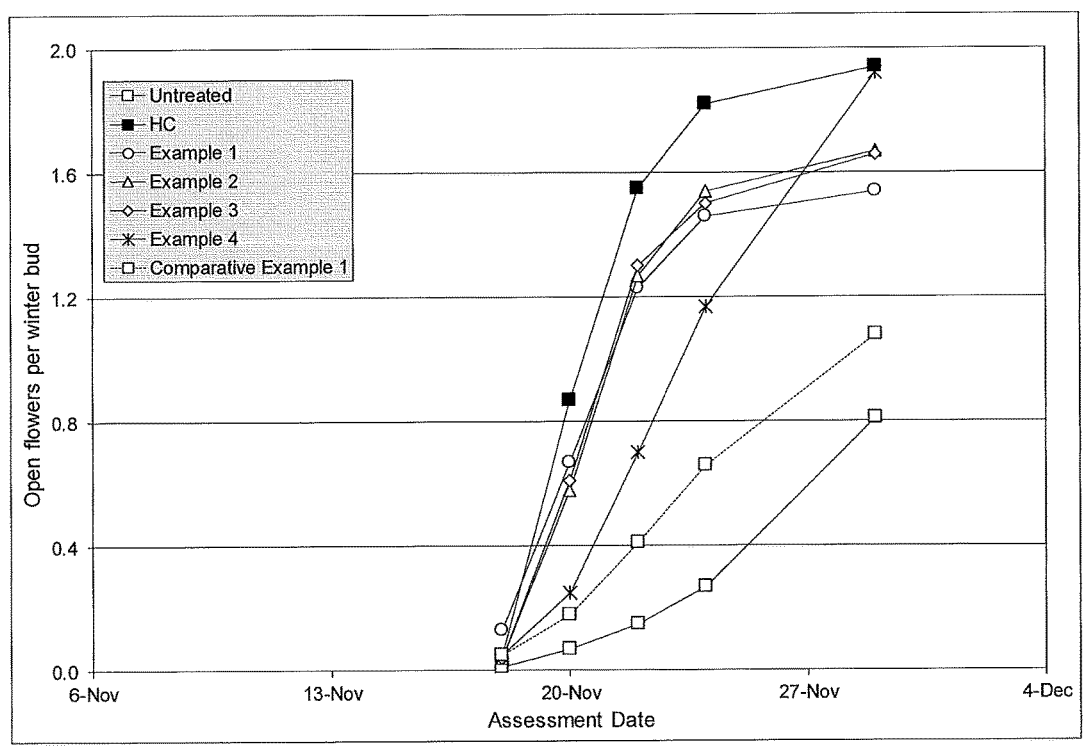
Figure 2. Progression of flowering in Trial 1.

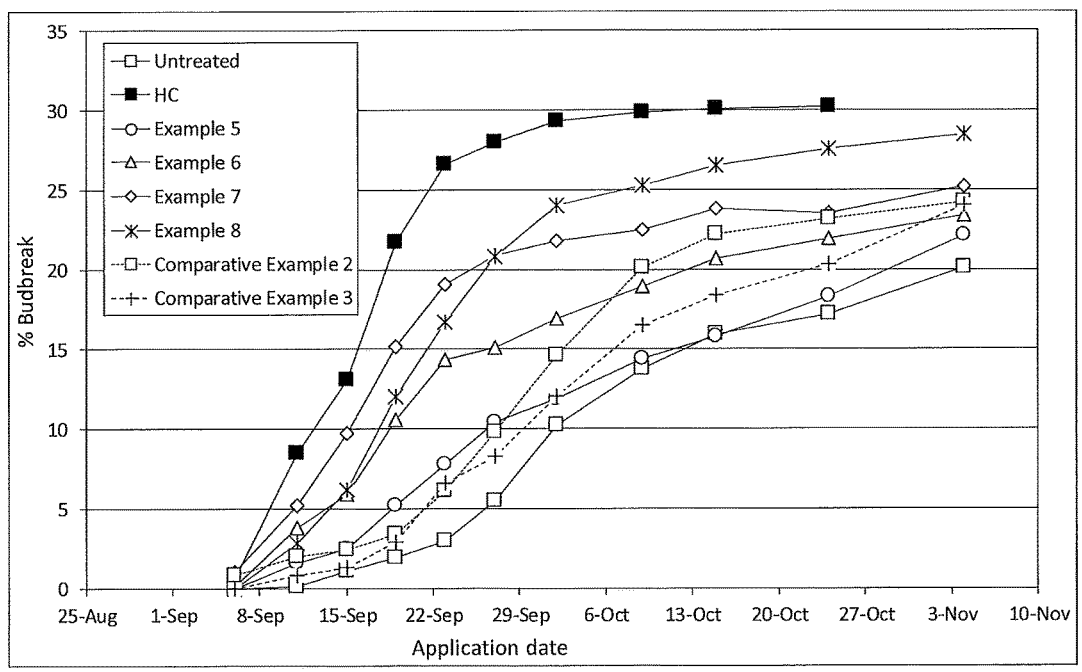
Figure 3. Progression of budbreak in Trial 2.

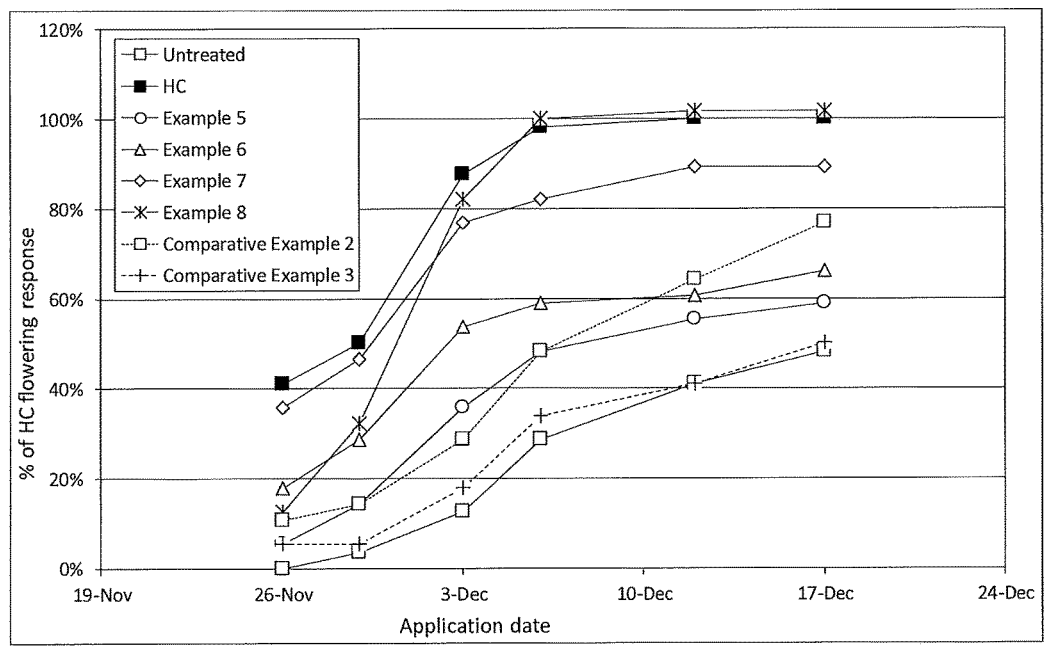
Figure 4. Progress of flowering in Trial 2.

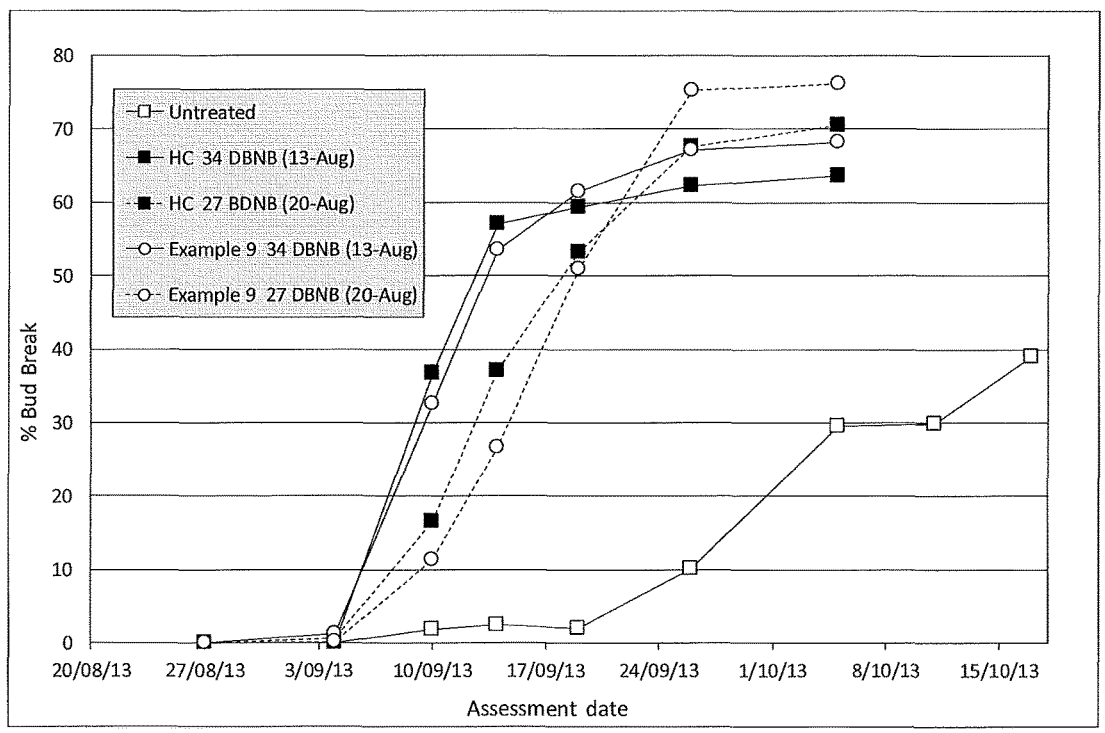
Figure 5. Progression of budbreak in Trial 4.

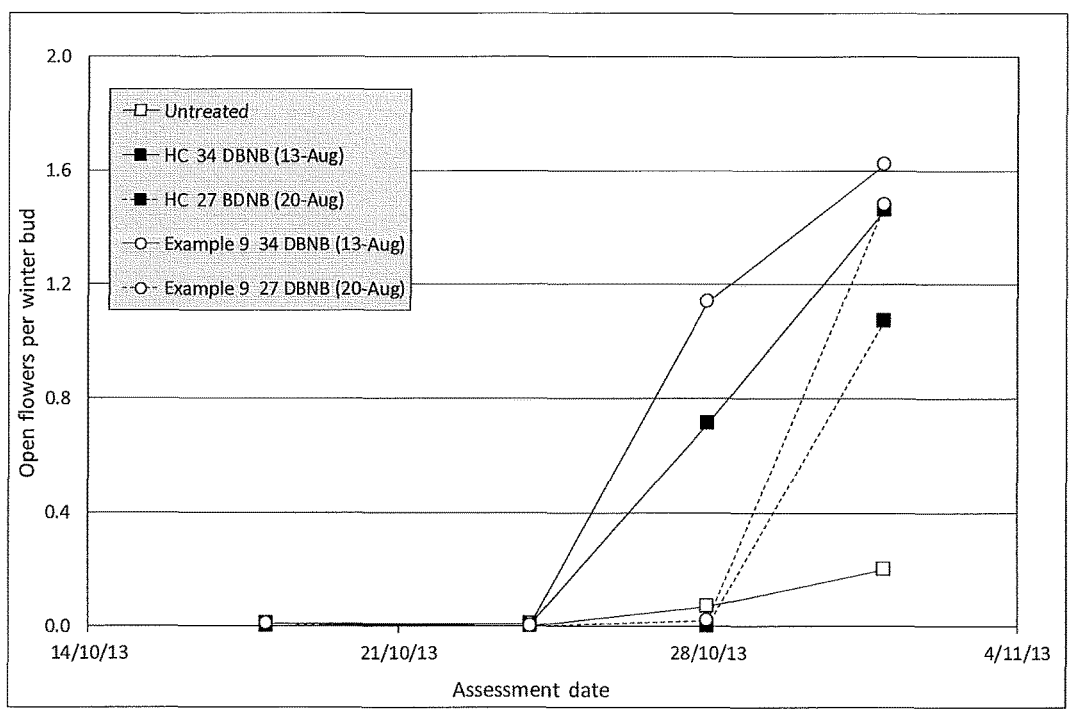
Figure 6. Progress of flowering in Trial 4.

Figure 7. Progression of budbreak in Trial 5.
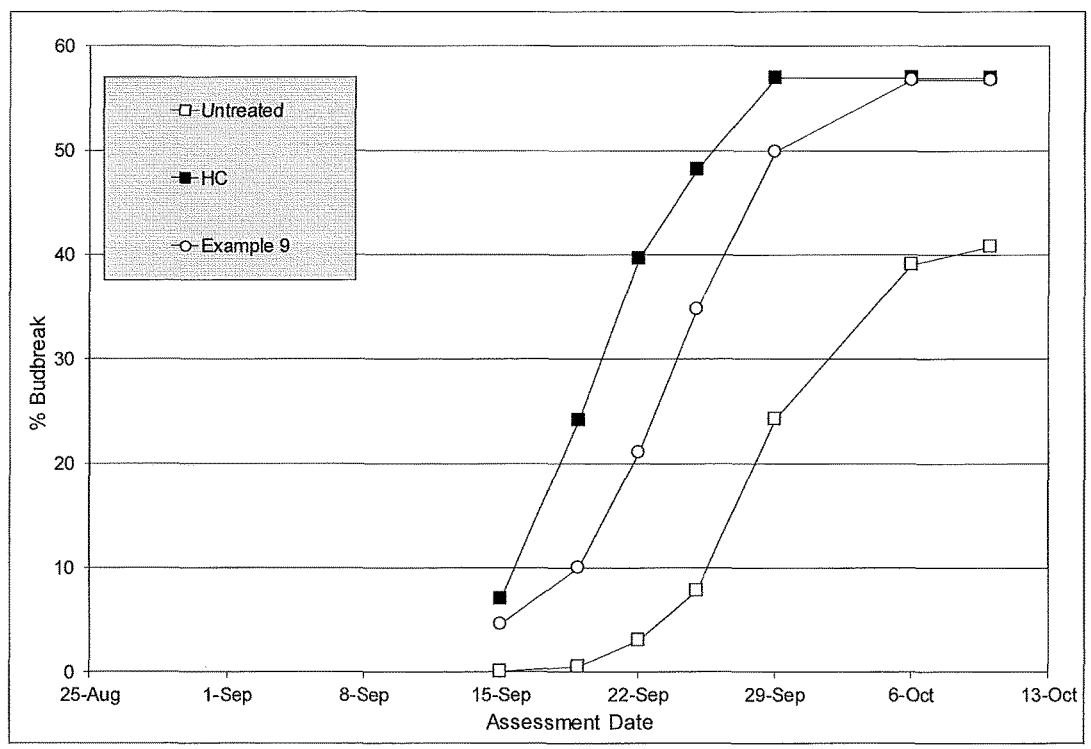

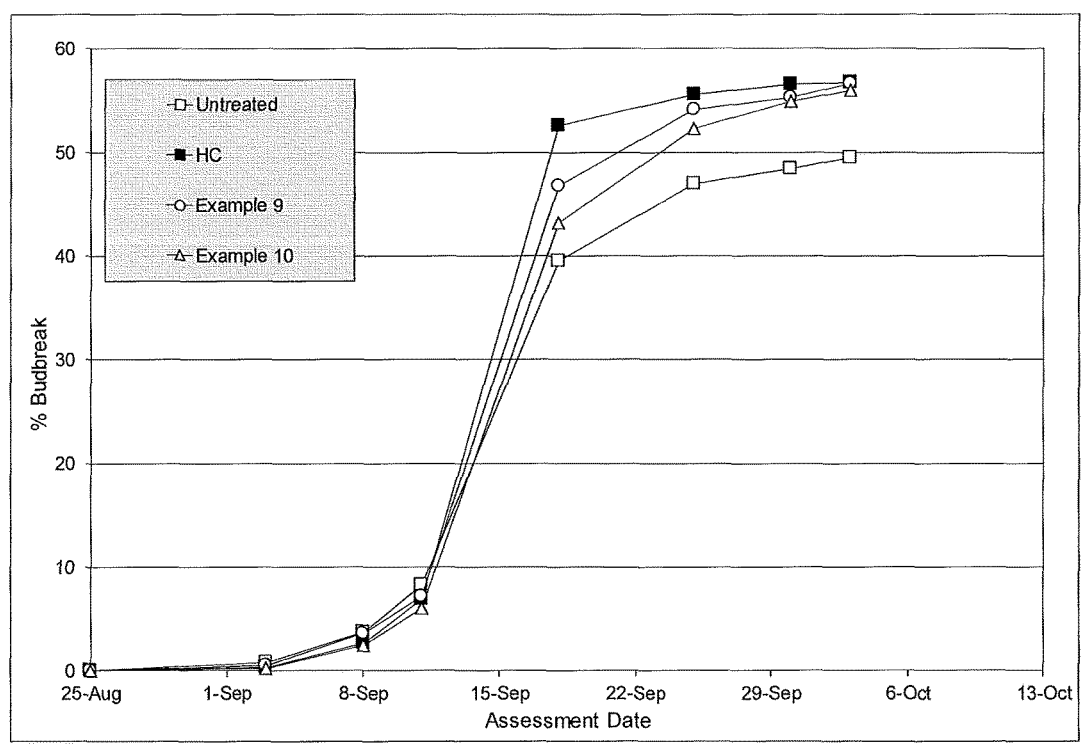
Figure 8. Progression of budbreak in Trial 6.

COMPOSITIONS FOR IMPROVING BUDBREAK AND FLOWERING

BACKGROUND

This invention relates to compositions formulated to improve budbreak, flowering and disease resistance in a variety of trees or crops including perennial fruit crops, to its method of preparation, and to its method of use.

Perennial horticultural and forestry plants native to temperate and boreal regions undergo cyclical periods of active growth and dormancy corresponding to the seasons. When growth resumes in spring the site of new growth is the bud. A dormant bud in a deciduous plant is sometimes called a "winter bud". Bud dormancy is characterised by a failure to grow even under favourable growth conditions, and the eventual resumption of growth is called dormancy break or "budbreak". The "depth of dormancy" is directly related to winter chill, which may be measured quantitatively by the accumulation of temperatures below a certain point, e.g. "Richardson Chill Units", or by average temperatures during the critical late autumn and winter months. Commercial growers working with cultivated plants want to obtain a strong budbreak followed by vigorous growth, flowering (and) fruit production. This occurs naturally when the plants with high chilling requirements experience a cold winter.

Many horticultural regions do not experience cold winters, and changes in local climatic conditions are increasingly exacerbating the problem of poor winter chill. It is possible to overcome the effects of poor winter chill and in some plants or to augment the benefits of good winter chill by chemical treatment of plants in the latter part of dormancy. The simplest chemical "budbreakers" are 4,6-dinitro-o-cresol, now deregulated in most countries, and hydrogen cyanamide (HC), which is still widely used in some countries. In certain crops, e.g. the main "Hayward" kiwifruit variety (*Actinidia deliciosa* (A. Chev.) C. F. Liang and A. R. Ferguson var. *deliciosa*), application of HC in late winter dormancy produces almost ideal results:

- Increase in % percentage of winter buds that break and develop shoots (% budbreak)
- Increase in uniformity of budbreak (i.e. more buds breaking at the same time and rate)
- Increase in flower numbers (therefore more fruit at harvest)
- Increase in the percentage of shoots bearing flowers (% floral shoots, preferable to increasing flower numbers by increasing the number of flowers per floral shoot)
- Condensed flowering (shortened flowering period, coinciding better with flowering of male vines therefore giving better pollination, and resulting in fruit reaching maturity in a synchronous fashion)
- Decrease in frequency of naturally occurring double and triple flowers (laterals), which produce undersized or malformed fruit, and must be removed manually at considerable cost to the grower.
- Control of green algae and lichen, an additional benefit unrelated to budbreak.

Unfortunately HC is a very toxic chemical and was excluded from Annex I to Directive 91/414/EEC in October 2008, and its continued use in non-European countries is under threat. The chief concerns are damage to non-target crops and human exposure, which can produce contact dermatitis, respiratory and gastrointestinal tract irritation, headaches, and liver damage when exposure is followed by alcohol consumption. In addition, in some crops HC produces too strong a response and can produce undesirable side effects. For example when applied to yellow-fleshed kiwifruit varieties such Hort16A (*Actinidia chinensis* Planch. var. *chinensis* 'Hort16A') and Gold3 (*Actinidia chinensis* Planch. var. *chinensis* 'Zesy002'), HC produces too many flowers and increases the frequency of unwanted lateral flowers. Safer budbreakers with more refined activity in plants are clearly needed.

SUMMARY

It is an object of the invention to provide an improved composition and/or preparative method thereof and/or use thereof which will obviate or minimize one or more of the previously mentioned disadvantages, or which will at least provide the public with a useful choice.

The inventor has unexpectedly discovered that compositions comprising:
one or more compounds represented by the structure:

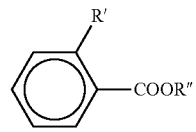

in which R' is OH or $OCOCH_3$, and R" is H, a monovalent cation, any C1-C10 alkyl group (saturated, unsaturated, linear or branched), any C7-C10 alkaryl group, or a phenyl group; an alkoxylated amine of the composition represented by the structure:

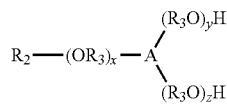

in which A is selected from N, $N^+R_1$, or N→O, and wherein $R_1$ is H, methyl or benzyl, $R_2$ is any C8-C22 alkyl group (saturated, unsaturated, linear or branched); $R_3$ is any C2-C4 alkyl group (linear or branched), x is in the range of 0 to 4 and y+z is in the range of 2 to 50; and, optionally, C6-C22 fatty acid esters and/or one or more nitrogen compounds, produce improved budbreak, improved flowering and/or increased disease resistance when applied to dormant perennial fruit crops.

The composition provides a safe and efficacious alternative to HC and minimises or eliminates one or more of the previously mentioned problems.

In one broad aspect this invention provides for a composition comprising:
(a) one or more compounds represented by the structure:

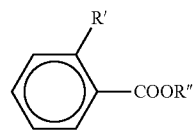

in which R' is OH or $OCOCH_3$, and R" is H, a monovalent cation, any C1-C10 alkyl group (saturated, unsaturated, linear or branched), any C7-C10 alkaryl group, or a phenyl group, and (b) an alkoxylated amine of the composition represented by the structure:

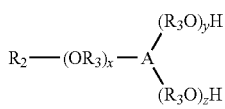

in which A is selected from N, $N^+R_1$, or $N\rightarrow O$, and wherein $R_1$ is H, methyl or benzyl, $R_2$ is any C8-C22 alkyl group (saturated, unsaturated, linear or branched); $R_3$ is any C2-C4 alkyl group (linear or branched), x is in the range of 0 to 4 and y+z is in the range of 2 to 50, and (c) optionally, one or more fatty acid esters comprising a C6-C22 fatty acid and a C1-C4 alcohol, and/or, (d) optionally one or more nitrogen compounds selected from urea, ammonium nitrate, calcium nitrate, calcium ammonium nitrate and potassium nitrate.

In a further broad aspect this invention provides methods of formulating the composition of the invention.

In a still further broad aspect this invention provides a method of improving budbreak, flowering and disease resistance using the composition of the invention.

In some aspects, a composition to produce improved budbreak, flowering and disease resistance in perennial fruit crops and/or ornamental trees, includes (a) one or more compounds represented by the structure:

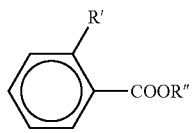

in which R' is OH or $OCOCH_3$, and R" is H, a monovalent cation, any C1-C10 alkyl group (saturated, unsaturated, linear or branched), any C7-C10 alkaryl group, or a phenyl group; and (b) an alkoxylated amine represented by the structure:

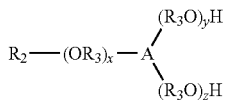

in which A is selected from N, $N^+R_1$, or $N\rightarrow O$, and wherein $R_1$ is H, methyl or benzyl, $R_2$ is any C8-C22 alkyl group (saturated, unsaturated, linear or branched), $R_3$ is any C2-C4 alkyl group (linear or branched), x is in the range of 0 to 4 and y+z is in the range of 2 to 50.

In some aspects, the compositions can further include (c) one or more fatty acid esters comprising a C6-C22 fatty acid and a C1-C4 alcohol. In other aspects, the compositions can further include (d) one or more nitrogen compounds selected from urea, ammonium nitrate, calcium nitrate, calcium ammonium nitrate and potassium nitrate. In some aspects, component (a) is salicylic acid or a salicylate comprising a monovalent cationic salt of salicylic acid, methyl salicylate, ethyl salicylate, isopropyl salicylate, allyl salicylate, butyl salicylate, isobutyl salicylate, 3-methyl-2-butenyl salicylate, isoamyl salicylate, pentyl salicylate, hexyl salicylate, cis-3-hexenyl salicylate, ethylhexyl salicylate, phenyl salicylate, benzyl salicylate, p-cresyl salicylate, phenethyl salicylate, 2-phenylpropyl salicylate, 3-phenylpropyl salicylate, or 2-acetoxysalicylate. For example, in some aspects, (a) is salicylic acid, a monovalent cationic salt of salicylic acid or methyl salicylate. In some aspects, the cation is an alkali metal ion, an ammonium ion, amine, a quaternary ammonium ion or an amine oxide.

In some non-limiting aspects, the compositions can include components (a) and (b) wherein (a) is salicylic acid, and (b) is an alkoxylated amine represented by the structure:

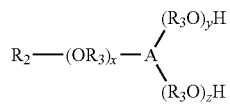

in which A is selected from N, $N^+R_1$ or $N\rightarrow O$, and, wherein $R_1$ is H, methyl or benzyl, $R_2$ is any C8-C22 alkyl group (saturated, unsaturated, linear or branched), $R_3$ is any C2-C4 alkyl group (linear or branched), x is in the range of 0 to 4 and y+z is in the range of 2 to 50.

In some aspects, the composition is configured for application to perennial fruit crops.

In other aspects, a composition for application to dormant perennial fruit crops to produce improved budbreak, flowering and disease resistance can include:

(a) one or more compounds represented by the structure:

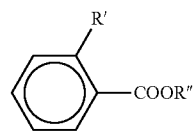

in which R' is OH or $OCOCH_3$, and R" is H, a monovalent cation, any C1-C10 alkyl group (saturated, unsaturated, linear or branched), any C7-C10 alkaryl group, or a phenyl group;

(b) an alkoxylated amine represented by the structure:

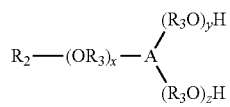

in which A is selected from N, $N^+R_1$, or $N\rightarrow O$, and wherein $R_1$ is H, methyl or benzyl, $R_2$ is any C8-C22 alkyl group (saturated, unsaturated, linear or branched), $R_3$ is any C2-C4 alkyl group (linear or branched), x is in the range of 0 to 4 and y+z is in the range of 2 to 50; and (c) one or more fatty acid esters comprising a C6-C22 fatty acid and a C1-C4 alcohol. In some aspects, this composition can further include (d) one or more nitrogen compounds selected from urea, ammonium nitrate, calcium nitrate, calcium ammonium nitrate and potassium nitrate.

In some aspects, the composition can be such that (a) is salicylic acid, (b) is an alkoxylated amine represented by the structure:

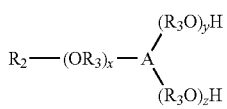

in which A is selected from N, N⁺R₁, or N→O, and wherein R₁ is H, methyl or benzyl, R₂ is any C8-C22 alkyl group (saturated, unsaturated, linear or branched), R₃ is any C2-C4 alkyl group (linear or branched), x is in the range of 0 to 4 and y+z is in the range of 2 to 50, and (c) is methyl oleate, ethyl oleate or butyl oleate.

In some aspects, (a) is present in an amount of about 0.1% to about 40% w/w; (b) is present in an amount of about 1% to about 99%; (c) is present in an amount of about 1% to about 80%; and (d) is present in an amount of about 1% to about 80%.

In some aspects, the compositions can further include a biocide selected from a bactericide, a fungicide, an insecticide or a nematicide.

In some aspects, a method for improving budbreak, flowering and disease resistance in perennial fruit crops and/or ornamental trees, includes applying to aerial plant parts physiologically effective amounts of a composition comprising:
(a) one or more compounds represented by the structure:

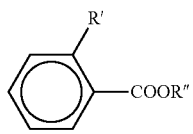

in which R' is OH or OCOCH₃, and R" is H, a monovalent cation, any C1-C10 alkyl group (saturated, unsaturated, linear or branched), any C7-C10 alkaryl group, or a phenyl group, and
(b) an alkoxylated amine represented by the structure:

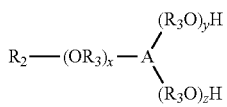

in which A is selected from N, N⁺R₁, or N→O, and wherein R₁ is H, methyl or benzyl, R₂ is any C8-C22 alkyl group (saturated, unsaturated, linear or branched), R₃ is any C2-C4 alkyl group (linear or branched), x is in the range of 0 to 4 and y+z is in the range of 2 to 50. In some aspects, the composition further includes (c) one or more fatty acid esters comprising a C6-C22 fatty acid and a C1-C4 alcohol and/or (d) one or more nitrogen compounds selected from urea, ammonium nitrate, calcium nitrate, calcium ammonium nitrate and potassium nitrate. Furthermore, in some aspects of the method, the composition is applied at an application rate in the range from about 5 kg/Ha to about 200 kg/Ha. The method can further include diluting the composition into water. In some aspects, applying the composition comprises spraying aerial plant parts during winter dormancy. In some aspects, the perennial fruit crops comprise vine fruits, berry fruits, pip fruits, stone fruits and nuts.

BRIEF DESCRIPTION OF THE DRAWINGS

The disclosure is accompanied by the following illustrative figures:

FIG. 1 illustrates the progression of budbreak in Trial 1;
FIG. 2 illustrates the progression of flowering in Trial 1;
FIG. 3 illustrates the progression of budbreak in Trial 2;
FIG. 4 illustrates the progress of flowering in Trial 2;
FIG. 5 illustrates the progression of budbreak in Trial 4;
FIG. 6 illustrates the progress of flowering in Trial 4;
FIG. 7 illustrates the progression of budbreak in Trial 5; and
FIG. 8 illustrates the progression of budbreak in Trial 6.

DETAILED DESCRIPTION

As stated above, the present disclosure relates to a composition for improving budbreak, flowering and disease resistance in a variety of trees or crops including perennial fruit crops, to its method of preparation, and to its method of use, which are now described in detail with accompanying figures. It is noted that like reference numerals refer to like elements across different embodiments.

The following definitions and abbreviations are to be used for the interpretation of the claims and the specification. As used herein, the terms "comprises," "comprising," "includes," "including," "has," "having," "contains" or "containing," or any other variation thereof, are intended to cover a non-exclusive inclusion. For example, a composition, a mixture, process, method, article, or apparatus that comprises a list of elements is not necessarily limited to only those elements but can include other elements not expressly listed or inherent to such composition, mixture, process, method, article, or apparatus.

As used herein, the articles "a" and "an" preceding an element or component are intended to be nonrestrictive regarding the number of instances (i.e. occurrences) of the element or component. Therefore, "a" or "an" should be read to include one or at least one, and the singular word form of the element or component also includes the plural unless the number is obviously meant to be singular.

As used herein, the terms "invention" or "present invention" are non-limiting terms and not intended to refer to any single aspect of the particular invention but encompass all possible aspects as described in the specification and the claims.

As used herein, the term "about" modifying the quantity of an ingredient, component, or reactant employed refers to variation in the numerical quantity that can occur, for example, through typical measuring and liquid handling procedures used for making concentrates or solutions. Furthermore, variation can occur from inadvertent error in measuring procedures, differences in the manufacture, source, or purity of the ingredients employed to make the compositions or carry out the methods, and the like. In one aspect, the term "about" means within 10% of the reported numerical value. In another aspect, the term "about" means within 5% of the reported numerical value. Yet, in another aspect, the term "about" means within 10, 9, 8, 7, 6, 5, 4, 3, 2, or 1% of the reported numerical value.

As used herein, the term budbreak (otherwise known as dormancy break) refers to the initiation of growth from a dormant bud at the beginning of the annual growth cycle. When applied to dormant perennial crops budbreakers improve budbreak and usually also affect downstream processes in a similar manner leading to improved flowering and fruiting. More specifically such improvements can include:
an increase in shoot, flower and/or fruit numbers, but in highly floral species or varieties a reduction may be desirable;

an advance in the onset of budbreak and flowering to achieve an earlier harvest, but sometimes a retardation is sought in order to avoid or reduce early spring frost damage;

a more rapid budbreak;

condensed flowering which, in turn, improves pollination, reduces disease susceptibility (flowering is often a time when protective sprays may not be applied), increases consistency in maturity indices to enable a single harvest and improve profitability;

improved synchronisation of flowering with male pollinators;

improved flower and fruit characteristics such as the absence of double and triple flowers/fruits that don't mature well; and more predictable timing of growth stages.

In addition, budbreaker compositions should be safe to use and in some aspects are not phytotoxic and not damaging to non-target crops and the environment.

Perennial fruit crops applicable to the invention can include vine fruits, berry fruits, pip fruits, stone fruits, and nuts. Included among vine fruits are wine and table grapes, passionfruit, kiwifruit, kiwi berries and the like. Included among berry fruits are *rubus* species (blackberries, raspberries, dewberries, tayberries and the like, as well as a very wide range of hybrid species such as boysenberries, loganberries, marionberries, etc.), *ribes* species (blackcurrants, redcurrants, gooseberries and a number of hybrid species), *vaccinium* species (cranberry, blueberry, huckleberry, etc.), and mulberry, tamarillos, figs and avocados. Pip fruits (or pome fruits) include apples, crab apples, pears, nashi, quince, loquats, persimmons, etc. Stone fruits include apricots, peaches, plums, nectarines, mangoes, cherries, olives, etc. Nuts include chestnuts, hazelnuts, walnuts, pistachios, almonds, hickory, pecans, etc.

The invention is also applicable to a wide range of ornamental trees where it is desirable to increase budbreak and flowering.

The composition comprises as a first component (referred to herein as component "(a)") one or more compounds represented by the structure:

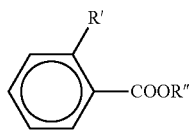

in which R' is OH or OCOCH$_3$, and R" is H, a monovalent cation, any C1-C10 alkyl group (saturated, unsaturated, linear or branched), any C7-C10 alkaryl group, or a phenyl group.

The compounds can be based on salicylic acid (2-hydroxybenzoic acid, C6H4(OH)COOH), a phytohormone isolated from plants and capable of acting as an elicitor. Salicylic acid is a plant hormone, a molecule present and active at very low concentrations, that is involved in a plant defence system against biotrophic pathogens called systemic acquired resistance (SAR), one of two well characterised systems of induced resistance. Plants also possess protective systems responsive to viruses, insect pests and abiotic stresses. In SAR exposure to a single biotrophic pathogen triggers a heightened state of defence against a broad range of biotrophic pathogens throughout the plant. Salicylic acid functions in individual responding cells as part of the "SA-dependent defence pathway" that ultimately activates a set of "salicylic acid-responsive" defence related genes. Molecules other than salicylic acid transmit the signal that alerts other (systemic) tissues to the presence of the pathogen. Salicylic acid applied externally to plant tissues at very low concentrations produces a similar response to pathogen exposure and, as such, acts as an "elicitor". SAR is a relatively rapid plant response associated with the active growth phase of the growth-dormancy cycle. Salicylic acid has the following physical properties: Molecular formula C$_7$H$_6$O$_3$; Molecular weight 138.12 g/mole; Form white needle-shaped fine crystals, odourless; m.p. 159° C.; f.p. 157° C.; v.p. 1.09×10$^{-8}$ MPa (25° C.); Density 1.443 g/ml (20° C.); K$_{ow}$ log P=2.26; pKa 2.98; Solubility in water 2.24 g/L (25° C.), benzene 0.775% w/w (25° C.), propanol 27.36% w/w (21° C.), ethanol 34.87% w/w (21° C.), acetone 396 (23° C.). Biodegradation of salicylic acid is rapid in Pahokee muck soil under varying agricultural practices.

Salts and esters of salicylic acid are sometimes referred to as salicylates. Salts and partial salts of salicylic acid may be prepared using any agriculturally suitable monovalent cation. Suitable cations may include but are not limited to alkali metal ions, ammonium ions, amines, quaternary ammonium ions, and amine oxides.

In some aspects, salicylic acid is present in the composition as an alkoxylated amine salt. In some aspects, esters of salicylic acid may include esters formed by reaction with the carboxylic acid moiety (i.e. 2-hydroxybenzoates like methyl salicylate) or at the 2-hydroxy group (i.e. benzoates like acetylsalicylic acid, 2-acetoxybenzoic acid). A number of suitable esters based on aliphatic or aromatic alcohols up to C10 are commercially available as perfuming agents, flavouring agents and medicaments. These include methyl salicylate (oil of wintergreen), ethyl salicylate, isopropyl salicylate, allyl salicylate, butyl salicylate, isobutyl salicylate, 3-methyl-2-butenyl salicylate, isoamyl salicylate, pentyl salicylate, hexyl salicylate, cis-3-hexenyl salicylate, ethylhexyl salicylate, phenyl salicylate, benzyl salicylate, p-cresyl salicylate, phenethyl salicylate, 2-phenylpropyl salicylate, 3-phenylpropyl salicylate. In some aspects, the salicylic acid ester is able to undergo spontaneous hydrolysis or metabolic conversion to salicylic acid and/or methyl salicylate.

In some aspects, the native compound is salicylic acid, the salt is an amine ethoxylate salt, and the ester is methyl salicylate. For example, an amine ethoxylate salt of salicylic acid can be used.

The alkoxylated amines of the composition, a second component of the invention (referred to herein as component "(b)"), are cationic surfactants represented by the structure:

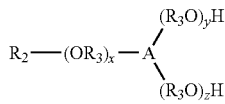

in which A is selected from N, N$^+$R$_1$, or N→O, and wherein R$_1$ is H, methyl or benzyl, R$_2$ is any C8-C22 alkyl group (saturated, unsaturated, linear or branched); R$_3$ is any C2-C4 alkyl group (linear or branched), x is in the range of 0 to 4 and y+z is in the range of 2 to 50.

The alkoxylated amine surfactants may be manufactured from any naturally occurring mixtures of fatty acids (plant oils, animal fats, etc), synthetic mixtures, semi-purified or purified fatty acids. A wide range of products suitable for the invention are commercially available. These include Tomamine® series ethoxylated ether amines such as Tomamine® E-17-5, ethoxylated quaternary ammonium compounds such as Tomamine® Q-17-5, and ethoxylated amine oxides such as Tomamine® AO-14-2, manufactured by Air Products and Chemicals Inc; Toximul® ethoxylated tallow amines from Stepan; Empilan® AM fatty amine ethoxylates from Huntsman; Ethomeen® ethoxylated amines, Ethoquad® ethoxylated quaternary ammonium salts, and Propomeen® propoxylated fatty amines from Akzo Nobel; and Genamin® fatty amine ethoxylates from Clariant, to name a few.

In some aspects, a further component of the composition can be one or more fatty acid esters comprising a C6-C22 fatty acid and a C1-C4 alcohol (referred to herein as component "(c)"). These compounds are available in bulk as mixtures of fatty acid esters wherein the heterogeneity reflects the fatty acid distribution of the oil or fat starting material, not the alcohol residue. Fatty acids are esterified and triglycerides transesterified using a single alcohol. Fatty acid methyl esters are now produced in large quantities as biodiesel. The monounsaturated omega-9 fatty acid oleic acid (18:1 cis-9) is the most abundant fatty acid in canola, palm and jatropha oils as well as animal fats, and accordingly fatty acid methyl esters derived from these sources are sometimes simply called methyl oleate. Longer chain alcohol residues up to C4 have the advantage of improving the bark penetration properties of the sprayed mixture. Various blends of ingredients such as, for example, methyl oleate and butyl oleate in any ratio ranging from about 1:0 to about 0:1 is encompassed within the composition of the invention. Other mixtures with different alcohol residues may be contemplated. In some aspects, the fatty acid ester is a fatty acid methyl ester.

Moreover, in some aspects, the compositions can contain at least one nitrogen compound (referred to herein as component "(d)"). The optional nitrogen compounds of the composition can include urea, ammonium nitrate, calcium nitrate, calcium ammonium nitrate and potassium nitrate, among others. The exact choice and concentration of nitrogen compounds depends on the target crop species. For example, with kiwifruit one mixture of compounds may be substituted for another with little effect on efficacy.

Suitable formulation types and methods of manufacture for the composition of this invention are described, for example, in "Chemistry and Technology of Agrochemical Formulations", 1998, D. A. Knowles (editor), Kluwer Academic Publishers, "Pesticide Formulation and Adjuvant Technology", 1966, C. L. Foy (editor), CRC Press, and "Formulation Technology: Emulsions, Suspensions, Solid Forms", 2001, H. Mollet and A. Grubenmann, Wiley-VCH.

For ease of use in the field concentrates of the composition are prepared ready for dilution into water, comprising components (a)+(b) or, alternatively, components (a)+(b)+ (c). In some aspects, component (d) is prepared as a separate liquid nitrogen concentrate for dilution into water. Simple mixing into water of the formulation concentrate of (a)+(b), or (a)+(b)+(c), along with the liquid nitrogen concentrate provides the simplest method to optimise ingredient concentrations in the field according to the crop species to be treated. The one or more nitrogen compounds of component (d) may alternatively be added directly to water in the spray tank as powdered solids, either before or after the addition of the abovementioned concentrates. The composition of the invention encompasses formulated concentrates comprising all of ingredients (a)-(d), and it includes the spray mixture prepared by any means including the separate addition of any of ingredients (a)+(b) and, optionally, (c) and/or (d).

Any suitable weight ratios may be utilized. For example, the following weight ratios of ingredient may be used when preparing concentrates of the composition comprising components (a), (b) and (c):

(a)+(b): about 0.1% to about 40% (a) and about 1% to about 99% (b).

(a)+(b)+(c): about 0.1% to about 40% (a), about 1% to about 99% (b), and about 1 to about 80% (c).

Further additives may be combined with any of the concentrate mixtures of the composition or with the spray mixture. Customary formulation additives and their functions are described in the previously mentioned publications. Such additives suitable for the present invention include water, agriculturally suitable cationic and anionic surfactants, dispersants, drift reduction agents, emulsifiers, penetrants, spreaders, wetting agents, soaps, carriers, oils, solvents, diluents, inert ingredients, conditioning agents, emollients, acids, bases, salts, organic and inorganic solid matrices of various kinds, preservatives, anti-foam agents, anti-freeze agents, stickers, binders, dyes, fertilizers, micronutrients, and the like.

Compositions comprising (a)+(b) can be prepared as non-aqueous soluble concentrates (formulation code SL). For example, component (a) is simply dissolved or mixed into component (b).

In one aspect, a composition including salicylic acid is used to titrate an alkoxylated amine surfactant in its basic form to prepare a neutral salt. Depending on the ratio of ingredients and the identity and concentration of component (a), a further, different acid may be required to complete the titration of an alkoxylated amine surfactant (in its basic form) to approximately neutral pH, or in some cases to reduce the pH of the resulting spray mixture to a value as low as about pH 3. Any agriculturally acceptable inorganic or organic acid may be used including but not limited to hydrochloric acid, sulphuric acid, phosphoric acid, nitric acid, formic acid, acetic acid, propionic acid, glycolic acid, lactic acid, succinic acid, citric acid, benzoic acid, oxalic acid, C1-C20 alkylsulphonic acids, arylsulphonic acids and disulphonic acids, C1-C20 alkylphosphonic acids, arylphosphonic acids and diphosphonic acids. Many alkoxylated amine surfactants are sold ready-for-use in neutralised form. When using these compounds with non-esterified salicylates several options are available to the formulator: (i) addition of salicylic acid to produce an acidic mixture; (ii) addition in any order of salicylic acid and a suitable base to produce a neutral mixture; (iii) addition of a salicylic acid salt to produce a neutral mixture. Salicylate esters may be mixed into either basic or neutralised alkoxylated amine surfactants, and the pH can be further adjusted by addition of any of the abovementioned acids or with a suitable base to achieve a targeted pH in the final spray mixture. Suitable bases include any agriculturally acceptable alkali metal hydroxide, ammonium hydroxide or an amine.

Depending on the degree and type of alkoxylation, some neat alkoxylated amine surfactants when mixed at high strength into water transition through a gelled state which can take a long time to fully disperse. The same problem can occur when diluting a formulation comprising (a)+(b) to prepare a spray mixture. This can be overcome when preparing the concentrate by mixing the alkoxylated amine surfactant (1-99% by volume) into a suitable diluent (1-99% by volume) such as water and/or a water-miscible non-aqueous solvent selected from but not limited to alcohols, glycols, glycol ethers and esters. In some aspects, the diluent is non-aqueous. Most salicylate esters are liquids and in many cases will act as suitable diluent without a further, separate diluent when present in amounts in excess of about 20% of the formulation.

In order to prepare formulation concentrates comprising components (a)+(b)+(c), it is necessary to overcome the incompatibility of fatty acid esters (hydrophobic) and alkoxylated amine surfactants (hydrophobic and polar/charged). This is generally brought about by introducing a strong organic acid containing a hydrophobic moiety to act as coupling agent between oil and amine surfactant. Examples of suitable known coupling agents include the strong organic acids including but not limited to C1-C20 alkylsulphonic acids, arylsulphonic acids, C1-C20 alkarylsulphonic acids and disulphonic acids, C1-C20 alkylphosphonic acids, arylphosphonic acids, C1-C20 alkarylphosphonic and diphosphonic acids, e.g. toluene sulphonic acid, xylene sulphonic acid, dodecyl benzene sulphonic acid (dobanic acid), etc.

Surprisingly, we have found that salicylic acid, a weak carboxylic acid, functions as a good coupling agent enabling the mixing of alkoxylated amine surfactants together with an oil, such as methyl oleate to prepare emulsifiable concentrates that disperse readily into water. The resulting oil in water emulsions are stable in the absence or presence of the high salt concentrations that occur when using the optional nitrogen compounds of the invention. When using salicylic acid to couple amine and oil, it can be combined with the amine in its basic form. Optionally a further organic strong acid may be added to fully neutralise the amine. The ingredients—salicylic acid, further organic strong acid, basic amine and oil may be combined in any order. For example, one can neutralise the basic amine before mixing in the oil component.

The invention provides a method of improving budbreak, flowering and disease resistance in perennial fruit crops which comprises applying to aerial plant parts physiologically effective amounts of the composition comprising:
(a) one or more compounds represented by the structure:

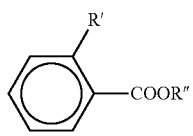

in which R' is OH or $OCOCH_3$, and R'' is H, a monovalent cation, any C1-C10 alkyl group (saturated, unsaturated, linear or branched), any C7-C10 alkaryl group, or a phenyl group;
(b) an alkoxylated amine of the composition represented by the structure:

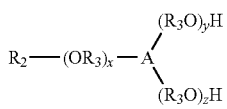

in which A is selected from N, $N^+R_1$, or N→O, and wherein $R_1$ is H, methyl or benzyl, $R_2$ is any C8-C22 alkyl group (saturated, unsaturated, linear or branched); $R_3$ is any C2-C4 alkyl group (linear or branched), x is in the range of 0 to 4 and y+z is in the range of 2 to 50; and
(c) optionally, one or more fatty acid esters comprising a C6-C22 fatty acid and a C1-C4 alcohol; and/or,
(d) optionally one or more nitrogen compounds selected from urea, ammonium nitrate, calcium nitrate, calcium ammonium nitrate and potassium nitrate.

The composition may be applied at any time during dormancy, depending on the crop species. Generally the optimal time of application is between about 2 weeks and about 10 weeks prior to the date of natural budbreak. Often, the composition is applied after winter pruning, although this is not an absolute requirement.

The composition can be applied at a rate ranging from about 1 kg per hectare (kg/ha) to about 300 kg/ha based on the combined weight of ingredients (a)+(b), (a)+(b)+(d), or (a)+(b)+(c)+(d). In some aspects, the composition can be applied at about 5 kg/Ha to about 200 kg/Ha based on the combined weight of ingredients. In some aspects, the application rate is about 10 kg/Ha to about 150 kg/Ha based on the combined weight of ingredients.

In general the composition may be diluted into water and applied by conventional means which in most cases will be spraying with an orchard air blast sprayer, although it may be more convenient with ornamentals, for example, to use a knapsack or motorised knapsack sprayer. The rate of water addition is determined by the crop in question, larger species requiring a greater water rate to ensure adequate coverage. Concentrate spraying is possible although super wetters commonly used with concentrate spraying must be used with extreme caution to avoid possible antagonism with the ingredients in the composition. Drift reduction agents may also be used provided they do not contain anionic surfactants and should be checked in a small scale trial prior to widespread use.

Biocidal active ingredients including fungicides, bactericides, insecticides, nematicides, and the like, may be combined with the spray mixture provided the formulation ingredients are compatible with the composition of the invention. Fertilizers other than those in component (d) may also be combined with the dilutions of the composition provided they do not substantially interfere with budbreak enhancing mode of action.

EXAMPLES

It will be appreciated that the following examples of compositions of the present invention and methods of use are provided as non-limiting examples only and that other compositions and methods of use will also fall within the ambit of the present invention.

Examples 1-4

| Component | Example 1 | Example 2 | Example 3 | Example 4 |
|---|---|---|---|---|
| Salicylic acid | 2.76 g | 2.76 g | — | 1.38 g |
| Methyl salicylate | — | — | 1.52 | — |
| Tomamine E-17-5 | 40.00 g | 40.00 g | 40.00 g | 6.67 g |
| Teric 12A3 | — | — | — | 6.67 g |
| Tensiofix XN6 | — | — | — | 6.67 g |
| Propylene glycol | 20.00 g | 20.00 g | 20.00 g | — |

-continued

| Component | Example 1 | Example 2 | Example 3 | Example 4 |
|---|---|---|---|---|
| Methyl oleate | — | — | — | 40.00 g |
| 5 mole/litre Hydrochloric acid | 12.80 g | 16.80 g | 16.60 g | — |
| Ammonium nitrate | 110.0 g | 110.0 g | 110.0 g | 110.0 g |
| Calcium ammonium nitrate | 110.0 g | 110.0 g | 110.0 g | 110.0 g |
| Water | To 2.0 litres | To 2.0 litres | To 2.0 litres | To 2.0 litres |
| Final pH | 6.6 | 3.8 | 6.6 | 2.9 |

Note:
Tomamine E-17-5 is an alkyl ether (C17 equivalent) tertiary amine modified with 5 moles of ethylene oxide, Teric 12A3 is an alcohol ethoxylate and Tensiofix XN6 a phosphate ester surfactant. The mixtures were prepared as liquid concentrates by first mixing the Tomamine E-17-5 with propylene glycol or the other surfactants, followed by slow addition of salicylic acid or methyl salicylate until dissolved, then HCl, and finally methyl oleate in Example 4. The concentrates are stable at ambient temperatures and may be combined with water and nitrogen salts in the field then made up to volume before use.

Examples 5-8

| Component | Example 5 | Example 6 | Example 7 | Example 8 |
|---|---|---|---|---|
| Salicylic acid | 2.45 g | 4.91 g | 7.36 g | 2.45 |
| Tomamine E-17-5 | 35.29 g | 36.05 g | 36.80 g | 35.38 |
| Propylene glycol | 17.65 g | 18.02 g | 18.40 g | — |
| Methyl oleate | — | — | — | 35.38 |
| Hydrochloric acid (5 mole/litre) | 6.65 g | 3.33 g | — | — |
| p-Toluenesulfonic acid (65%) | — | — | — | 7.98 |
| Ammonium nitrate | 110.0 g | 110.0 g | 110.0 g | 110.0 g |
| Calcium ammonium nitrate | 110.0 g | 110.0 g | 110.0 g | 110.0 g |
| Water | To 2.0 litres | To 2.0 litres | To 2.0 litres | To 2.0 litres |
| Final pH | 7.6 | 7.6 | 7.6 | 7.5 |

Note:
The mixtures were prepared in the same manner as Examples 1-4.

Examples 9-12

| Component | Example 9 | Example 10 | Example 11 | Example 12 |
|---|---|---|---|---|
| Salicylic acid | 7.36 g | 7.36 g | 7.00 g | 7.00 g |
| Tomamine E-17-5 | 36.80 g | 36.80 g | 34.99 g | 34.99 g |
| Propylene glycol | 18.40 g | 18.40 g | — | — |
| Methyl oleate | — | — | 34.99 g | 34.99 g |
| Urea | 89.0 g | — | 89.0 g | — |
| Calcium ammonium nitrate | 105.0 g | — | 105.0 g | — |
| Water | To 2.0 litres | To 2.0 litres | To 2.0 litres | To 2.0 litres |
| Final pH | 7.2 | 7.2 | 7.2 | 7.2 |

Note:
The mixtures were prepared in the same manner as Examples 1-4.

Comparative Example 1

The following mixture is based on the use of Armobreak™ as disclosed in U.S. Pat. No. 5,885,932, which is hereby incorporated by reference in its entirety. Armobreak™ is a tallowamine containing five moles of ethylene oxide derived units and 12 moles of propylene derived oxide units. In 2.0 litres of water mix 40.00 g Armobreak™, 110 g ammonium nitrate and 110 g calcium ammonium nitrate, final pH 6.7.

Comparative Example 2

In 2.0 litres of water mix 40.00 g Armobreak™, and 110 g potassium nitrate, final pH 9.4.

Comparative Example 3

The following mixture is based on EP 1,189,513, which is hereby incorporated by reference in its entirety. EP 1,189,513 lists Valagro S.p.A. as proprietor and relates to a composition utilizing, among other things, a non-ionic surfactant. For example, EP 1,189,513 discloses a composition comprising ammonium nitrate and nonylphenol made to react with ethylene oxide. Valagro® markets compositions under the trade name Erger® K and Active Erger®. Erger® is a mineral fertilizer designed to be sprayed on dormant wood prior to bud break. In 2.0 litres of water mix 120 ml Erger® K and 180 ml Active Erger®, final pH 6.7.

Comparative Example—Hydrogen Cyanamide (HC)

A commercial preparation of HC was diluted at 60 ml per litre of water in combination with a drift reduction agent (Driftstop™—a blend of an organosilicone surfactant and synthetic polymer drift retarding agents) (2 ml/litre).

All trials were based on a randomized complete block experimental design.

TRIAL 1: Trial 1 demonstrates the superior performance of compositions of the invention compared to a prior art HC-alternative. A cane painting experiment was performed in a Hayward kiwifruit orchard in the Bay of Plenty New Zealand in 2010 following a winter with average winter chill. Low-medium vigour canes of 1.6 m average length from 36 vines were tagged and either left untreated or painted with one of HC, Examples 1-4 and Comparative Example 1. The date of painting (6-Aug) was 56 days before natural budbreak (DBNB). Budbreak (BBCH stage 9) and flowering (BBCH stage 60) were determined based on the photographs published by Salinero et al., 2009, "Phenological growth stages of kiwifruit (*Actinidia deliciosa* 'Hayward')", Scientia Horticulturae 121, 27-31, which is hereby incorporated by reference in its entirety. Graphed and tabulated data represent averages of the 36 replicates and are normalised based on the number of winter buds on each cane.

FIG. 1 illustrates the progression of budbreak in Trial 1. FIG. 2 illustrates the progression of flowering in Trial 1. The progress curves depicted in FIGS. 1 and 2 were fitted to a cumulative normal curve to calculate the midpoints of budbreak and flowering (the dates corresponding to a 50% response) and spread of response time (defined as 4× standard deviation) as summarised in Tables 1 and 2. Compared to untreated results, HC and Examples 1-3 all produced large increases in budbreak and flowering, and they advanced the onset and reduced the spread of budbreak and flowering. The oil containing mixture of Example 4 produced slightly later and slower responses than HC and Examples 1-3 but was still considerably more effective than Comparative Example 1.

TABLE 1

Onset and rapidity of budbreak in Trial 1.

|  | Midpoint of BB | Spread of BB | Advance in Midpoint | Reduction in Spread |
|---|---|---|---|---|
| Untreated | 11-Oct | 48 | 0 | 0 |
| HC | 25-Sep | 17 | 16 | 32 |
| Example 1 | 25-Sep | 20 | 16 | 28 |
| Example 2 | 26-Sep | 19 | 15 | 29 |
| Example 3 | 26-Sep | 19 | 15 | 30 |
| Example 4 | 1-Oct | 29 | 10 | 19 |
| Comp. Example 1 | 2-Oct | 50 | 9 | −1 |

TABLE 2

Onset and rapidity of flowering in Trial 1.

|  | Midpoint of BB | Spread of BB | Advance in Midpoint | Reduction in Spread |
|---|---|---|---|---|
| Untreated | 26-Nov | 16 | 0 | 0 |
| HC | 20-Nov | 7 | 6 | 9 |
| Example 1 | 20-Nov | 8 | 6 | 8 |
| Example 2 | 20-Nov | 7 | 6 | 9 |
| Example 3 | 20-Nov | 7 | 6 | 9 |
| Example 4 | 23-Nov | 12 | 3 | 4 |
| Comp. Example 1 | 23-Nov | 13 | 3 | 3 |

TRIAL 2: Trial 2 demonstrates the dose-response relationship between the concentration of the salicylic acid component and the budbreak and flowering responses in Hayward kiwifruit vines. A cane painting experiment was performed in 2012 in a Hayward kiwifruit orchard in Taranaki, New Zealand. Canes of 1.2 m average length from 33 vines were tagged and either left untreated or painted with one of HC, Examples 5-8 and Comparative Examples 2 and 3 on 9-Aug, 50 DBNB (28-Sep). Midpoints and spread were calculated for budbreak (Table 3) but there were insufficient data to perform the calculations for flowering. The orchard experienced extremely low winter chill and untreated canes produced a very poor budbreak, which HC improved considerably (FIG. 3). Increasing concentrations of salicylic acid (examples 5-7) produced progressively larger increases in the total number of buds broken, and progressively earlier budbreak, with reduced spread. Example 8 produced a strong response even though salicylic acid was present at a relatively low concentration, possibly reflecting the greater ability of oil containing compositions to penetrate the bark of kiwifruit canes. Comparative Example 2 produced a similar response to some examples of the present invention, whereas Comparative Example 3 barely produced any change compared to the untreated response. FIG. 3 illustrates the progression of budbreak in Trial 2. FIG. 4 illustrates the progress of flowering in Trial 2.

TABLE 3

Onset and rapidity of budbreak in Trial 2.

|  | Midpoint of BB | Spread of BB | Advance in Midpoint | Reduction in Spread |
|---|---|---|---|---|
| Untreated | 25-Sep | 26 | 0 | 0 |
| HC | 13-Sep | 19 | 12 | 7 |
| Example 5 | 24-Sep | 42 | 1 | −16 |
| Example 6 | 17-Sep | 33 | 7 | −7 |
| Example 7 | 14-Sep | 22 | 11 | 4 |
| Example 8 | 17-Sep | 25 | 8 | 1 |
| Comp. Example 2 | 23-Sep | 26 | 2 | 0 |
| Comp. Example 3 | 24-Sep | 32 | 0 | −6 |

TRIAL 3: Trial 3 demonstrates the utility of the invention in reducing disease following application in a Psa-infected orchard. A trial in which whole Hayward kiwifruit vines were sprayed was established in the Bay of Plenty in 2013. There were twelve replicates and two sets of untreated vines. HC (700 litres/Ha) and the composition of Example 8 (800 litres/Ha) were applied on three dates using a boom sprayer designed to produce spray deposition typical of an orchard air blast sprayer. Of particular interest in this trial was the prevalence of Psa leaf spotting that became evident in late spring, particularly in the early HC-sprayed vines. Vines were assessed for Psa leaf spotting by rating 40 randomly selected leaves (10 on each side of the two leaders that made up each vine) on a 1-5 scale (Table 4). ANOVA indicated a significant increase in leaf spotting in HC treated vines after the first two applications whereas treatment with Example 8 produced a slight decrease at all application dates.

TABLE 4

Psa leaf spotting in Hayward kiwifruit leaves

|  | Leaf spotting score | % Incidence |
|---|---|---|
| Untreated 1 | 0.21 bc | 10.4 bcd |
| Untreated 2 | 0.16 bc | 8.3 cd |
| HC 15-Aug (46 DBNB) | 1.15 a | 51.5 a |
| HC 24-Aug (37 DBNB) | 0.42 b | 21.7 b |
| HC 30-Aug (31 DBNB) | 0.31 bc | 18.3 bc |
| Example 8 9-Aug (52 DBNB) | 0.14 c | 8.3 cd |
| Example 8 16-Aug (45 DBNB) | 0.09 c | 5.0 d |
| Example 8 23-Aug (38 DBNB) | 0.13 c | 6.3 cd |

Means followed by same letter do not significantly differ (P = .05, Duncan's New MRT)

TRIAL 4: Trial 4 demonstrates the effectiveness of a composition of the invention as a budbreaker in Gold3 kiwifruit. This cane painting experiment was performed in a Bay of Plenty orchard in 2013 following a winter with poor chill in the key months of May and June. Low-medium vigour canes typical of the orchard were painted with either HC or Example 9 on 13-Aug and 20-Aug, 34 and 27 days before natural budbreak which occurred on 16-Sep. The composition of Example 9 advanced budbreak and condensed it as much as HC (Table 5 and FIG. 5). FIG. 5 illustrates the progression of budbreak and FIG. 6 illustrates the progress of flowering in Trial 4.

TABLE 5

Onset and rapidity of budbreak in Trial 4.

|  | Midpoint of BB 28-Sep | Spread of BB 41 | Advance in Midpoint 0.0 | Reduction in Spread 0 |
|---|---|---|---|---|
| HC 34 DBNB (13-Aug) | 9-Sep | 12 | 19 | 30 |
| HC 27 BDNB (20-Aug) | 14-Sep | 24 | 15 | 17 |
| Example 9 34 DBNB (13-Aug) | 10-Sep | 17 | 19 | 25 |
| Example 9 27 DBNB (20-Aug) | 16-Sep | 23 | 13 | 18 |

Like HC, the composition of Example 9 produced large increases in the key parameter, king flowers per winter bud (KFWB), by increasing % budbreak, by increasing the proportion of floral shoots and by increasing the number of king flowers per floral shoot (KFFS, Table 6). However, HC increased the frequency of lateral flowers (doubles and triples), which must be removed manually at considerable cost to the grower in order to ensure proper fruit sizing. In contrast, Example 9 produced no change in the frequency of laterals and deformed fruit (13-Aug) or eliminated them altogether (20-Aug).

TABLE 6

Summary of budbreak and flowering data for Trial 4.

|  | % Budbreak | KFWB | Floral shoots | KFFS | % Laterals | % Deformed |
|---|---|---|---|---|---|---|
| Untreated | 40.7 | 0.50 | 52% | 2.17 | 1.3 | 0.2 |
| HC 34 DBNB (13-Aug) | 64.5 | 1.48 | 83% | 2.90 | 9.9 | 1.7 |
| HC 27 BDNB (20-Aug) | 72.1 | 1.19 | 71% | 2.35 | 1.8 | 0.2 |
| Example 9 34 DBNB (13-Aug) | 68.9 | 1.58 | 82% | 2.80 | 1.3 | 0.1 |
| Example 9 27 DBNB (20-Aug) | 78.3 | 1.53 | 77% | 2.63 | 0.0 | 0.0 |

TRIALS 5 and 6: Trials 5 and 6 demonstrate the utility of the composition of the invention in promoting budbreak and flowering after poor and good winter chill, respectively. These 2014 sprayed trials were performed in the Bay of Plenty (Trial 5, five replicates, each a bay comprising two vines with ten assessment canes per rep, five on each side of the bay) and Hawkes Bay, NZ (Trial 6, four replicates, each a bay comprising four vines with twenty assessment canes per rep, five from each vine). HC (700 litres/Ha) and Examples 9 and 10 (800 litres/Ha) were sprayed on 16-Aug (37 DBNB, Trial 5) and 11-Aug (30 DBNB, Trial 6). FIG. 7 illustrates the progression of budbreak in Trial 5 and FIG. 8 illustrates the progression of budbreak in Trial 6.

Under current management practices Gold3 growers require at least about 1.8 single flowers per winter bud (SFWB) to achieve the recommended packout of 17,000 trays/Ha. After the poor winter chill of 2014 untreated vines in the Bay of Plenty orchard produced insufficient king flowers (1.7 KFWB, Table 7) to achieve targeted fruit yields, even with the costly option of snipping the pedicle to remove laterals leaving the king flower intact. HC treatment produced excessive flower numbers and nearly doubled the frequency of double and triple flowers, whereas Example 9 produced a moderate increase without producing more laterals. The advantage in this instance is the reduced thinning cost of cutting at the peduncle to remove all doubles and triples. The relatively good winter chill in Hawkes Bay produced adequate flower numbers in untreated vines but a very high frequency of laterals that was further increased by HC treatment. Treatment with Example 9, or with Example 10 which lacked the Nitrogen compounds, produced modest increases in flower numbers without increasing laterals thus greatly reducing thinning costs.

TABLE 7

Summary of budbreak and flowering data for Trial 5

|  | % Budbreak | KFWB | SFWB | % Laterals | % Double flowers | % Triple flowers |
|---|---|---|---|---|---|---|
| Untreated | 40.8 | 1.7 | 1.3 | 10.5 | 7.2 | 3.3 |
| HC | 56.9 | 3.1 | 2.5 | 18.7 | 14.4 | 4.3 |
| Example 9 | 56.7 | 2.4 | 2.0 | 10.4 | 8.0 | 2.4 |

TABLE 8

Summary of budbreak and flowering data for Trial 6

|  | % Budbreak | KFWB | SFWB | % Laterals |
|---|---|---|---|---|
| Untreated | 46.7 | 2.44 | 1.9 | 22.0 |
| HC | 55.9 | 2.61 | 1.8 | 31.2 |

TABLE 8-continued

Summary of budbreak and flowering data for Trial 6

|  | % Budbreak | KFWB | SFWB | % Laterals |
|---|---|---|---|---|
| Example 9 | 55.0 | 2.87 | 2.3 | 20.9 |
| Example 10 | 54.3 | 2.52 | 2.1 | 18.4 |

Trial 7: Use of the invention improved budbreak, flowering and hence fruit quality in Magnus variety blackcurrants following a winter with significant winter chill in Nelson, New Zealand in 2014. Examples 9 and 10 were sprayed at 500 l/Ha onto 20 m long rows on 21 August. On 17 December fruit were harvested from 5 canes per treatment and graded into black (target maturity), coloured (near mature) and green (immature, unsaleable). The weight distributions between black, coloured and green fruit were: untreated—60%, 33% and 7%; example 9-81%, 17% and 2%, example 10-94%, 6% and 0%.

Trial 8: Use on Granny Smith Apples was evaluated in New Plymouth, New Zealand following a poor winter chill in 2013. Treatments were applied on 9 Aug. 2013 at 200 L/Ha using a manual backpack sprayer in a replicated trial (4 replications of two tree plots). Example 12, which lacks the optional nitrogen compounds, produced enhanced budbreak and flowering compared to the untreated control, and approximately doubled fruit set compared to hydrogen cyanamide as a comparative example (HC in Table 9).

TABLE 9

Budbreak, flowering and fruit set on fruiting spurs of Granny Smith Apples.

| | % Budbreak 28 DAA | % Budbreak 39 DAA | % Budbreak 47 DAA | % Flowering 54 DAA | % Fruit set 74 DAA |
|---|---|---|---|---|---|
| Example 11 | 0 | 21 | 37 | 25 | 13 |
| Example 12 | 0 | 38 | 43 | 51 | 35 |
| HC | 14 | 39 | 34 | 66 | 16 |
| Untreated | 0 | 5 | 22 | 15 | 20 |

Having generally described this invention, including the best mode thereof, those skilled in the art will appreciate that the present invention contemplates the embodiments of this invention as defined in the following claims, and equivalents thereof. However, those skilled in the art will appreciate that the scope of this invention should not be measured merely by the specific embodiments exemplified herein.

Those skilled in the art will also appreciate that more sophisticated technological advances will likely appear subsequent to the filing of this document with the Patent Office. To the extent that these later developed improvements embody the operative principles at the heart of the present disclosure, those improvements are likewise considered to come within the ambit of the following claims.

The Invention may also broadly be said to consist in the parts, elements and features referred or indicated in the specification, individually or collectively, and any or all combinations of any of two or more parts, elements, members or features and where specific integers are mentioned herein which have known equivalents such equivalents are deemed to be incorporated herein as if individually set forth.

It will also be understood that where a product, method or process as herein described or claimed and that is sold incomplete, as individual components, or as a "Kit of Parts", that such exploitation will also fall within the ambit of the invention.

In an embodiment the invention includes within its scope a kit of parts, the kit of parts providing for a budbreaker composition in separate containers or as separate compartments within the same container a combination of:
(a) one or more compounds represented by the structure:

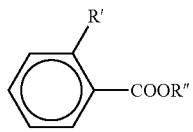

in which R' is OH or OCOCH$_3$, and R" is H, a monovalent cation, any C1-C10 alkyl group (saturated, unsaturated, linear or branched), any C7-C10 alkaryl group, or a phenyl group, and
(b) an alkoxylated amine of the composition represented by the structure:

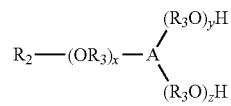

in which A is selected from N, N$^+$R$_1$, or N→O, and wherein R$_1$ is H, methyl or benzyl, R$_2$ is any C8-C22 alkyl group (saturated, unsaturated, linear or branched); R$_3$ is any C2-C4 alkyl group (linear or branched), x is in the range of 0 to 4 and y+z is in the range of 2 to 50, and
(c) optionally, one or more fatty acid esters comprising a C6-C22 fatty acid and a C1-C4 alcohol, and/or,
(d) optionally one or more nitrogen compounds selected from urea, ammonium nitrate, calcium nitrate, calcium ammonium nitrate and potassium nitrate.

The invention claimed is:
1. A composition formulated to produce improved budbreak, flowering and disease resistance in perennial fruit crops and/or ornamental trees, comprising:
(a) one or more compounds represented by the structure:

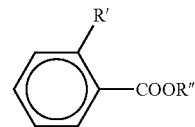

in which R' is OH or OCOCH$_3$, and R" is H, a monovalent cation, any saturated, unsaturated, linear or branched C1-C10 alkyl group, any C7-C10 alkaryl group, or a phenyl group, present in the composition in an amount of from about 0.1% to about 40%;
(b) an alkoxylated amine represented by the structure:

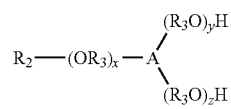

in which A is selected from N, N$^+$R$_1$, or N→O, and wherein R$_1$ is H, methyl or benzyl, R$_2$ is any saturated, unsaturated, linear or branched C8-C22 alkyl group, R$_3$ is any linear or branched C2-C4 alkyl group, x is in the range of 0 to 4 and y+z is in the range of 2 to 50; and
(d) one or more nitrogen compounds selected from the group consisting of urea, ammonium nitrate, calcium nitrate, calcium ammonium nitrate and potassium nitrate;
wherein the composition has a pH of about 3 to 7.6.
2. The composition according to claim 1, wherein (a) is salicylic acid or a salicylate comprising a monovalent cationic salt of salicylic acid, methyl salicylate, ethyl salicylate, isopropyl salicylate, allyl salicylate, butyl salicylate, isobutyl salicylate, 3-methyl-2-butenyl salicylate, isoamyl salicylate, pentyl salicylate, hexyl salicylate, cis-3-hexenyl salicylate, ethylhexyl salicylate, phenyl salicylate, benzyl salicylate, p-cresyl salicylate, phenethyl salicylate, 2-phenylpropyl salicylate, 3-phenylpropyl salicylate, or 2-acetoxysalicylate.

3. The composition according to claim 1, wherein (a) is salicylic acid, a monovalent cationic salt of salicylic acid or methyl salicylate.

4. The composition according to claim 1, wherein the cation is an alkali metal ion, an ammonium ion, amine, a quaternary ammonium ion or an amine oxide.

5. The composition according to claim 1, wherein
(a) is salicylic acid, and
(b) is an alkoxylated amine represented by the structure:

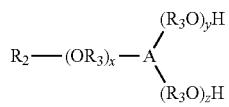

in which A is selected from N, $N^+R_1$ or $N{\rightarrow}O$, and wherein $R_1$ is H, methyl or benzyl, $R_2$ is any saturated, unsaturated, linear or branched C8-C22 alkyl group, $R_3$ is any linear or branched C2-C4 alkyl group, x is in the range of 0 to 4 and y+z is in the range of 2 to 50.

6. The composition according to claim 1, wherein the composition is formulated for application to perennial fruit crops.

7. The composition according to claim 1, wherein
(a) is salicylic acid, and
(b) is an alkoxylated amine represented by the structure:

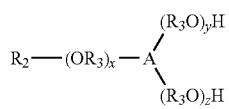

in which A is selected from N, $N^+R_1$, or $N{\rightarrow}O$, and wherein $R_1$ is H, methyl or benzyl, $R_2$ is any saturated, unsaturated, linear or branched C8-C22 alkyl group, $R_3$ is any linear or branched C2-C4 alkyl group, x is in the range of 0 to 4 and y+z is in the range of 2 to 50.

8. The composition according to claim 1, wherein (b) is present in an amount of about 1% to about 99%.

9. The composition according to claim 1, wherein (d) is present in an amount of about 1% to about 80%.

10. The composition according to claim 1, further comprising
(c) one or more fatty acid esters comprising a C6-C22 fatty acid and a C1-C4 alcohol.

11. The composition according to claim 10, wherein (c) is present in an amount of about 1% to about 80%.

12. A method for improving budbreak, flowering and disease resistance in perennial fruit crops and/or ornamental trees, comprising applying to aerial plant parts physiologically effective amounts of a composition comprising:
(a) one or more compounds represented by the structure:

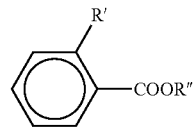

in which R' is OH or $OCOCH_3$, and R" is H, a monovalent cation, any saturated, unsaturated, linear or branched C1-C10 alkyl group, any C7-C10 alkaryl group, or a phenyl group, present in the composition in an amount of from about 0.1% to about 40%,
(b) an alkoxylated amine represented by the structure:

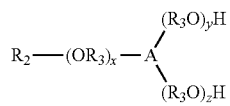

in which A is selected from N, $N^+R_1$, or $N{\rightarrow}O$, and wherein $R_1$ is H, methyl or benzyl, $R_2$ is any saturated, unsaturated, linear or branched C8-C22 alkyl group, $R_3$ is any linear or branched C2-C4 alkyl group, x is in the range of 0 to 4 and y+z is in the range of 2 to 50; and
(d) one or more nitrogen compounds selected from the group consisting of urea, ammonium nitrate, calcium nitrate, calcium ammonium nitrate and potassium nitrate;
wherein the composition has a pH of about 3 to 7.6.

13. The method according to claim 12, wherein the composition is applied at an application rate in the range from about 5 kg/Ha to about 200 kg/Ha.

14. The method according to claim 12, further comprising:
diluting the composition into water.

15. The method according to claim 12, wherein applying the composition comprises spraying aerial plant parts during winter dormancy.

16. The method according to claim 12, wherein the perennial fruit crops are selected from the group consisting of vine fruits, berry fruits, pip fruits, stone fruits and nuts.

17. The method according to claim 12, wherein the composition further comprises (c) one or more fatty acid esters comprising a C6-C22 fatty acid and a C1-C4 alcohol.

* * * * *